United States Patent
Franinovic et al.

(10) Patent No.: US 10,912,497 B2
(45) Date of Patent: Feb. 9, 2021

(54) DETECTION AND EVALUATION OF MOVEMENTS OF A USER

(71) Applicants: TYROMOTION GMBH, Graz (AT); ETH ZÜRICH, Zürich (CH); UNIVERSITÄT ZÜRICH, Zürich (CH); ZÜRCHER HOCHSCHULE DER KÜNSTE, Zürich (CH)

(72) Inventors: Karmen Franinovic, Zürich (CH); Dinis Meier, Zürich (CH); Samuel Bauer, Zürich (CH); Roger Gassert, Wetzikon (CH); Yeongmi Kim, Innsbruck (AT); Kaspar Leuenberger, Zürich (CH); Andreas Luft, Uitikon Waldegg (CH); Jeremia Held, Zürich (CH)

(73) Assignees: TYROMOTION GMBH, Graz (AT); ETH ZÜRICH, Zürich (CH); UNIVERSITÄT ZÜRICH, Zürich (CH); ZÜRCHER HOCHSCHULE DER KÜNSTE, Zürich (CH)

( * ) Notice: Subject to any disclaimer, the term of this patent is extended or adjusted under 35 U.S.C. 154(b) by 233 days.

(21) Appl. No.: 15/754,165

(22) PCT Filed: Aug. 23, 2016

(86) PCT No.: PCT/EP2016/069870
§ 371 (c)(1),
(2) Date: Feb. 21, 2018

(87) PCT Pub. No.: WO2017/032765
PCT Pub. Date: Mar. 2, 2017

(65) Prior Publication Data
US 2018/0235519 A1 Aug. 23, 2018

(30) Foreign Application Priority Data
Aug. 24, 2015 (CH) ..................... 1216/15

(51) Int. Cl.
*A61B 5/11* (2006.01)
*A61B 5/0488* (2006.01)
*A61B 5/00* (2006.01)

(52) U.S. Cl.
CPC .......... *A61B 5/1124* (2013.01); *A61B 5/0004* (2013.01); *A61B 5/0488* (2013.01);
(Continued)

(58) Field of Classification Search
CPC .......... A61B 5/00; A61B 5/11; A61B 5/1123; A61B 5/1124; A61B 5/4082; A61B 5/681;
(Continued)

(56) References Cited

U.S. PATENT DOCUMENTS

2006/0052727 A1* 3/2006 Palestrant ............. A61B 5/1118
600/595
2014/0378872 A1* 12/2014 Hong ..................... A61B 5/112
600/595
(Continued)

FOREIGN PATENT DOCUMENTS

WO 2014/113143 A1 7/2014
WO WO-2014113143 A1 * 7/2014 ............. G16H 50/20
WO 2014/207294 A1 12/2014

OTHER PUBLICATIONS

International Search Report issued in International Patent Application No. PCT/EP2016/069870, dated Nov. 28, 2016.

*Primary Examiner* — Eric F Winakur
(74) *Attorney, Agent, or Firm* — Medler Ferro Woodhouse & Mills PLLC

(57) ABSTRACT

A device for detecting and evaluating movements of a user comprises a processing unit, a data memory, a sensor unit with at least one biometric sensor, and a fastening device for fastening the sensor unit on an arm of the user. The processing unit is configured to detect movement data from movement signals generated by the sensor unit and to store
(Continued)

the movement data in the data memory. The device further comprises an evaluation module with which secondary movement data, which represent passive arm movements of the user, are filterable out of the movement data. The device enables the detection and evaluation of movements of an arm of the user in an efficient way.

20 Claims, 2 Drawing Sheets

(52) U.S. Cl.
CPC ............... *A61B 5/11* (2013.01); *A61B 5/112* (2013.01); *A61B 5/1112* (2013.01); *A61B 5/1118* (2013.01); *A61B 5/486* (2013.01); *A61B 5/681* (2013.01); *A61B 5/725* (2013.01); *A61B 5/7207* (2013.01); *A61B 5/7257* (2013.01); *A61B 5/742* (2013.01); *A61B 5/7405* (2013.01); *A61B 5/746* (2013.01); *A61B 5/7455* (2013.01); *A61B 5/1123* (2013.01); *A61B 5/6824* (2013.01); *A61B 2505/09* (2013.01); *A61B 2562/0219* (2013.01); *A61B 2562/0223* (2013.01); *A61B 2562/0247* (2013.01)

(58) Field of Classification Search
CPC ... A61B 5/6824; A61B 5/0004; A61B 5/0488; A61B 5/1112; A61B 5/1118; A61B 5/112; A61B 5/486; A61B 5/7207; A61B 5/725; A61B 5/7257; A61B 5/7405; A61B 5/742; A61B 5/7455; A61B 5/746
USPC ........................................................ 600/595
See application file for complete search history.

(56) References Cited

U.S. PATENT DOCUMENTS

2015/0190084 A1\* 7/2015 Johansson .............. G16H 10/20
  600/301
2015/0198460 A1\* 7/2015 Yamato ................. A61B 5/1118
  702/160

\* cited by examiner

DETECTION AND EVALUATION OF MOVEMENTS OF A USER

TECHNICAL FIELD

The invention relates to a device according to the preamble of independent claim 1 and a method according to the preamble of independent claim 13.

Such devices, which comprise a processing unit, a data memory, a sensor unit with at least one biometric sensor, and a fastening device for fastening the sensor unit on an arm of the user, wherein the processing unit is configured to detect movement data from movement signals generated by the sensor unit and to store the movement data in the data memory, may be used for detecting and evaluating movements of a user.

BACKGROUND OF THE INVENTION

In therapy or during training of persons, it is important in many applications to detect and evaluate movements by the persons. For example, in recent years, diverse devices have entered the market for measuring the activities of athletes or those interested in fitness. These devices measure and document various parameters, for example, the number of steps, distance travelled, which is determined, for example, based on Global Positioning System (GPS) data, or pulse. With the increasing miniaturization of sensors, additional sensors will certainly be added in the future.

However, there is often a need for more specific movements by the person in therapy or during training. For example, during therapy for stroke patients, it is especially important that the affected person trains certain body parts. In particular, the most common result of a stroke is that the affected person experiences one-sided paralysis of the body. Rehabilitation may last several years and requires a lot of discipline and perseverance. To achieve progress, the affected body parts must be moved daily with intense effort. Impaired arms are overlooked particularly often in daily use.

However, the above mentioned devices are not suited for detecting and evaluating the movements of specific body parts, in particular of arms and fingers.

Therefore, the underlying object of the present invention is to propose a device or a method with which the movements of an arm of a user may be detected and evaluated in an efficient way.

BRIEF SUMMARY OF THE INVENTION

The object is achieved according to the invention by a device as defined in independent claim 1, and by a method as defined in independent claim 13. Advantageous alternative embodiments of the invention arise from the dependent claims.

The essence of the invention consists in the following: a device for detecting and evaluating movements of a user comprises a processing unit, a data memory, a sensor unit with at least one biometric sensor, and a fastening device for fastening the sensor unit on an arm of the user. The processing unit is configured to detect movement data from movement signals generated by the sensor unit and to store the movement data in the data memory. The device additionally comprises an evaluation module, by means of which secondary movement data, which represent passive arm movements of the user, are filterable out of the movement data.

In conjunction with the invention, the term "arm" may relate to arms of a person in a broad sense. It may thereby include in particular both the upper arm, elbow, and lower arm and also the wrist, hand, and fingers.

The term, "passive arm movement", may relate to a movement of the arm of the user, which is generated by an unspecified movement of the body of the user, or as concomitant movement. For example, a passive arm movement may be a movement of the arm which is induced by a movement of the entire body, as is exerted, for example, by a transport means on the entire body of the user, including the arm. Or a passive arm movement may also result from a total movement of the body or the movement of another body part of the body of the user. In particular, a passive arm movement may be generated, for example, by a walking movement of the user.

In contrast, the term, "active arm movement" can relate to a targeted movement of the arm of the user. For example, targeted arm movements might be those which function for manipulating an object or the like.

The processing unit may comprise a processor (CPU) and a memory (Random Access Memory (RAM)). It may be configured for detecting and storing movement data, in that it executes a computer program that carries out the corresponding steps or functions. It may also be correspondingly programmed. The processing unit may also be switched for this purpose or may, for example, be configured as a switch, which satisfies these steps and functions.

The evaluation module may be comprised by the processing unit or implemented by the same. In particular, the processing unit may be programmed so that it implements the evaluation module.

The evaluation module makes it possible that, from the movement signals detected by the device, those may be identified which are assigned to an active arm movement. In particular, all movement data which are triggered by a passive arm movement may be removed from movement signals detected by means of the sensor unit. Correspondingly, the device is capable of excluding arm and/or hand movement from the movement data and making this available to the user. This may be of considerable use for the user, for example if arm and/or hand function is impaired by an illness or accident. This may also help the user to understand how he/she used a hand or arm during a certain time or whether it was inactive. In particular, a comparison of the use of the left and right arms is also possible. Thus, the device enables the detection and evaluation of the movements of an arm of the user in an efficient way.

The device preferably comprises a warning device, wherein the processing unit is configured to evaluate the filtered movement data and to activate the warning device if the evaluated movement data do not exceed a predefined threshold value across a predefined rest period. In this way, the user may be informed about inactivity, which may increase training efficiency.

The warning device preferably comprises a graphic display, a speaker, a vibrating structure, a muscle stimulator, or a combination thereof. The user may be efficiently informed by such a warning device. The device preferably comprises a mounting means for fastening the warning device on a finger or the ball of a thumb of the user. Such a mounting means enables a comfortable, secure putting on or taking off by the user.

The evaluation module preferably comprises a high-pass filter and/or a low-pass filter, by means of which the movement data may be pre-filtered. Such a high-pass filter or low-pass filter enables the removal of small-scale interfering signals or upward and downward outliers. The efficiency of the device may be further increased as a result. The high-pass filter or the low-pass filter of the evaluation module is preferably set to a value between 0.1 Hz and 1 Hz, and particularly to a value of approximately 0.3 Hz. Using such an adjusted high-pass filter or low-pass filter, many movement data may be filtered out which are either of no importance or of secondary importance for the evaluation.

The evaluation module is preferably configured in such a way to continuously calculate magnitudes or integrals of the movement data. The magnitudes or integrals or areas may relate to a curve of the movement data. The movement data preferably comprise values of movements in three directions of a three-dimensional coordinate system per time point, and the magnitudes preferably correspond in each case to the square root of the sum of the squares of the values in the three directions for the same time point.

The evaluation module is preferably configured to process the magnitudes calculated from the movement data in a window function. The term, "window function", relates in this context to a function for frequency analysis, which determines the weight with which sample values, obtained during a sampling of a signal within a section or window, are entered in subsequent calculations. Such window functions are generally known. The window function may advantageously be a Hamming window function.

The evaluation module is preferably configured to identify periodic patterns in the magnitudes, which are processed using the window function, by means of Fourier transformation (FT) and in particular fast Fourier transformation (FFT). The term "fast Fourier transformation" or FFT is understood in this case to be a known algorithm for calculating the discrete Fourier transformation (DFT), with which a digital signal may be broken down into its frequency components and these may then be analysed. By using a fast Fourier transformation, periodic patterns in the frequency data or the magnitudes may be efficiently determined.

The evaluation module is thereby preferably configured to count steps, in case a periodic pattern is identified. The evaluation module is also preferably configured to count arm activities, in case no periodic pattern is identified. In this way, the movement data may be efficiently sorted or separated into movements caused by walking and other arm movements. Thus, either steps or arm movements may be counted in a specified period or in a specified window of the movement data; however, not both. This may enable an efficient, targeted evaluation.

The evaluation module or the processing unit is preferably configured to calculate an activity count, which corresponds to the sum of all magnitudes or integrals in a predefined time window. The activity count may be defined in a reference unit. A movement may correspond to a gripping of a door latch or an appliance. The activity count may enable a simple evaluation of the arm movements of the user. It may thus be taken into account, in particular, that a plurality of relatively small movements are evaluated identically to a lower number of relatively large movements.

The predefined time window lies preferably in a range from 0.5 seconds to ten minutes, and in particular in a range from two seconds to five minutes. This enables an efficient, purposeful calculation of the movement data and determination of the activity count.

Preferably, the at least one biometric sensor of the sensor unit comprises an accelerometer, a gyroscope, a magnetometer, a pressure sensor, a GPS sensor, a muscle activity sensor such as an EMG muscle sensor, or a combination of the same. The term, "EMG muscle sensor", may, in this context, relate to a sensor for electromyography (EMG), with which the electrical muscle activity is detected. An active arm movement may be efficiently detected and evaluated with such biometric sensors.

The fastening device is preferably configured for fastening the sensor unit on a finger of the user. Movements of the fingers may thus be evaluated.

The device preferably comprises an interface adapter for connecting to a computer. The computer may be a desktop computer, a laptop computer, a tablet computer, a smartphone, or something similar. The interface adapter is preferably a radio interface adapter for wireless connection to the computer. Data may be efficiently transmitted to the computer with such a device. The data may be further evaluated or displayed or stored on the computer.

The sensor unit is preferably adjusted for sampling at a frequency of at least 10 Hz or at least 20 Hz and in particular for a range of approximately 50 Hz to approximately 100 Hz. Sampling at such a frequency enables an efficient detection and evaluation of arm movements.

Another aspect of the invention relates to a method for detecting and evaluating movements of a user. The method comprises the following steps: fastening a sensor unit on an arm of the user, wherein the sensor unit has at least one biometric sensor; detecting movement data from movement signals generated by the sensor unit; storing the movement data in a data memory; and filtering secondary movement data, which represent passive arm movements of the user, out from the movement data. The filtered movement data may be, in particular, primary movement data. The effects and advantages described above in conjunction with the device may be efficiently realized using such a method and the subsequently described preferred embodiments. The method may be implemented by a computer program, which comprises commands for the execution thereof, when the computer program runs on the device.

The method preferably comprises an evaluation of the filtered movement data, and a warning of the user if the evaluated movement data do not exceed a predefined threshold value over a predefined rest period. The warning may comprise a display of visual information, an acoustic alarm, a vibration, or a combination thereof.

The method preferably comprises a high-pass filtration carried out prior to filtering out the secondary movement data. The high-pass filtration is preferably carried out at 0.3 Hz.

During the filtering out of secondary movement data, magnitudes or integrals of the movement data are preferably continuously calculated. During calculation of the magnitudes or integrals of the movement data per time point, each magnitude preferably corresponds to the square root of the sum of the squares of values in three directions of a three-dimensional coordinate system. The method includes in a preferred way a calculation of an activity count, which corresponds to the sum of all magnitudes or integrals in a predefined time window. The predefined time window lies preferably in a range from 0.5 seconds to ten minutes, and in particular in a range from two seconds to five minutes.

The at least one biometric sensor of the sensor unit preferably comprises an accelerometer, a gyroscope, a magnetometer, a pressure sensor, or a combination of the same. During the method, the sensor unit is preferably fastened on a finger of the user. The method preferably comprises a transmission of the filtered-out movement data to a computer.

During the method, the sensor unit is preferably adjusted for sampling at a frequency of at least 10 Hz or at least 20 Hz and in particular for a range of approximately 50 Hz to approximately 100 Hz.

The method preferably additionally comprises the following steps: Fastening a further sensor unit on a second arm of the user, wherein the further sensor unit has at least one biometric sensor; detecting further movement data from movement signals generated by the further sensor unit; storing the further movement data in a data memory; filtering secondary movement data out from the further movement data; and comparing the filtered-out movement data to the filtered-out further movement data. In this way, arm movements of the two arms may be compared with each other. This makes it possible to draw further conclusions about the progress of the arm movements and provides the user with more understanding.

The method preferably comprises a definition of a movement goal, in particular a daily or weekly movement goal, and a depiction of a degree of achievement of the movement goal. In this way, the user may be efficiently motivated to maintain the movement goal, by means of which improved progress is made possible. The movement goal may be automatically defined on the basis of stored movement data, and in particular may be automatically adjusted upward.

BRIEF DESCRIPTION OF THE DRAWINGS

Further advantageous variants of the invention will become clear from the following description of exemplary embodiments of the invention, which refers to the schematic drawing. In particular, the device according to the invention and the method according to the invention are subsequently described in detail with reference to the attached drawings on the basis of exemplary embodiments. Shown are.

DETAILED DESCRIPTION OF EMBODIMENTS OF THE INVENTION

Figure 1:
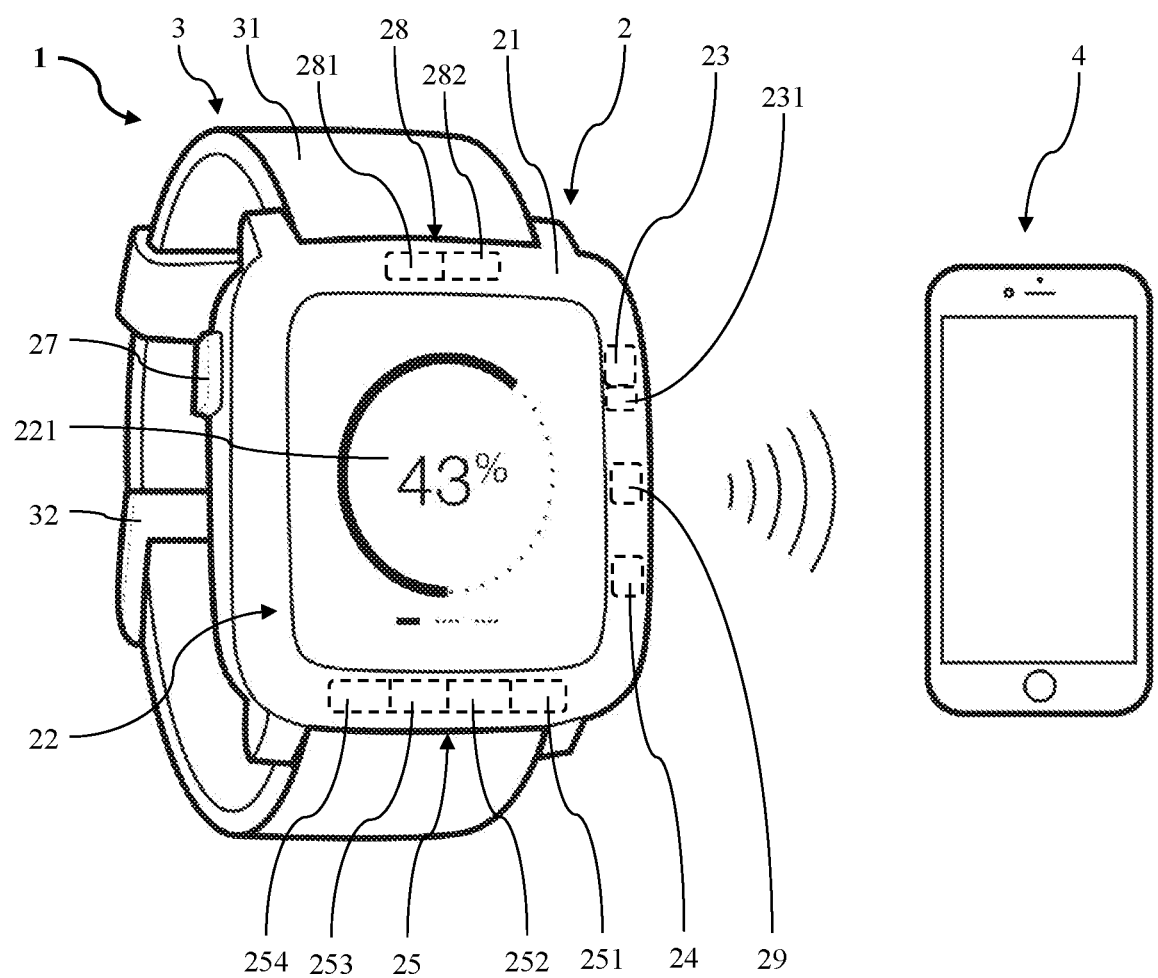
FIG. 1: a perspective view of one exemplary embodiment of a device according to the invention and a smartphone connected thereto.

Certain expressions are used in the following description for practical reasons and must not be construed as limiting. The words "right", "left", "down" and "up" designate directions in the drawing to which reference is made. The expressions "inwardly", "outwardly", "beneath", "above", "to the left of", "to the right of", or the like are used to describe the arrangement of designated parts relative to one another, the movement of designated parts relative to one another, and the directions toward or away from the geometric center of the device and the listed parts of the same as shown in the figures. These relative spatial indications also comprise other positions and orientations other than the ones depicted in the figures. For example, if a part depicted in the figures is rotated, then elements or features described as "below" are then "above". The terminology encompasses the words expressly mentioned above, derivatives thereof, and words of similar meaning.

In order to avoid repetitions in the figures and in the associated description of the different aspects and exemplary embodiments, certain features should be understood as common to different aspects and exemplary embodiments. The omission of an aspect from the description or from a figure does not mean that this aspect is lacking in the associated exemplary embodiment. Instead, such an omission may be made for the sake of clarity and for avoiding repetitions. In this regard, the following specification applies to the entire further description: If reference signs are present in a figure for the sake of graphic clarity but not mentioned in the directly associated descriptive text, then reference shall be made to the explanation thereof in preceding figure descriptions. Furthermore, if reference signs are mentioned in the descriptive text directly associated with a figure but are not present in the associated figure, reference shall be made to the preceding and following figures. Similar reference signs in two or more figures stand for similar or identical elements.

FIG. 1 shows a device 1 according to the invention with a functional part 2 and an armband 3 as the fastening device and as the mounting means. Functional part 2 comprises a housing 21 in which a display 22 is embedded as a visual display. A processing unit 23, a data memory 24, a sensor unit 25, a warning device 28, and a radio interface adapter 29 are arranged in the interior of housing 21. Housing 21 is equipped on the left side with a push button 27, via which the functional part may be operated by a user.

Sensor unit 25 comprises multiple biometric sensors, namely a GPS sensor 251, a gyroscope 252, an accelerometer 253, and a magnetometer 254. Warning device 28 comprises a speaker 282, a vibrator 281, and display 22. Processing unit 23 is programmed to implement an evaluation module 231.

Armband 3 comprises a plastic band 31 and a closure 32. Using closure 32, plastic band 31 may be adjusted in length so that device 1 with sensor unit 25 may be fastened on a wrist of the user.

Figure 2:
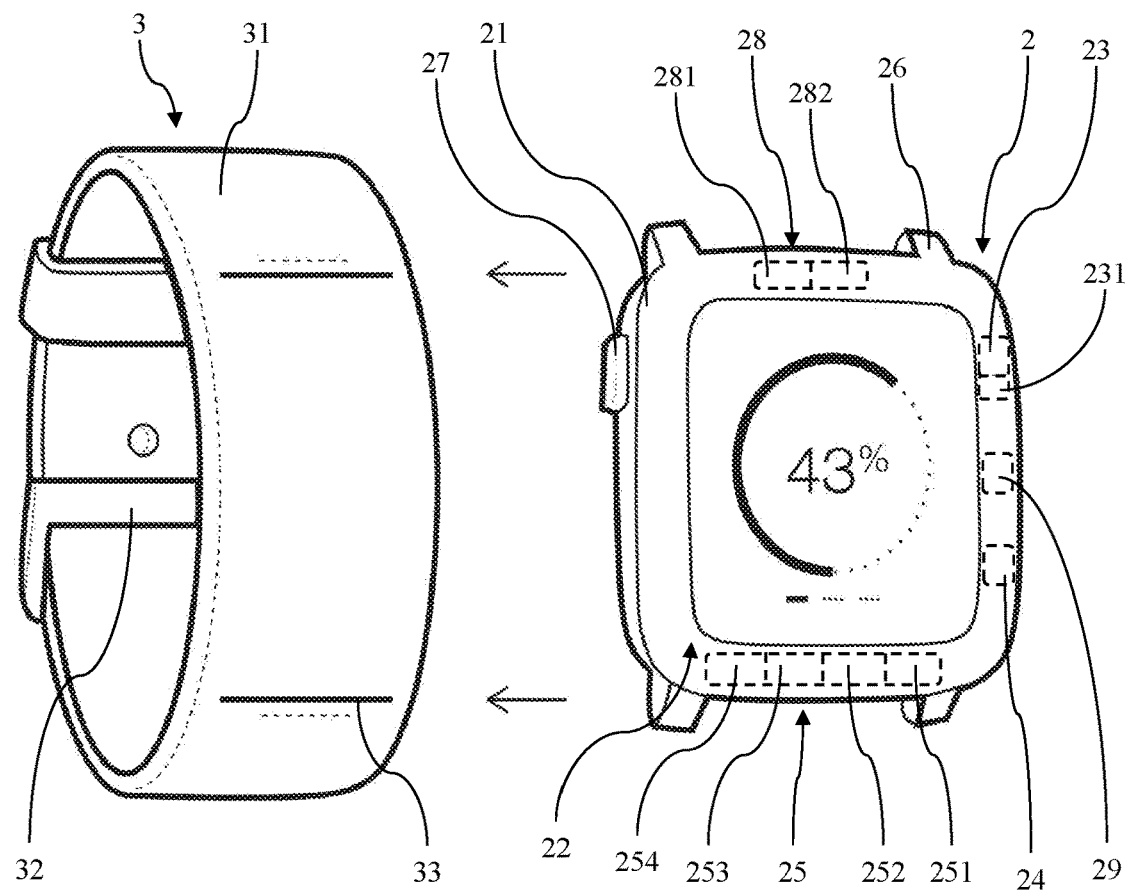
FIG. 2: a perspective view of the device from FIG. 1 in a separated state.

As is shown in FIG. 2, functional unit 2 may be separated from armband 3 and remounted on it. For this purpose, housing 21 has a clip structure 26 and plastic band 31 has a clip guide 33. Clip structure 26 comprises two upper and two lower clamping parts, wherein plastic band 21 may be laterally clamped between two of the clamping parts.

During operation, device 1 is fastened on the wrist of the user and the biometric sensors of sensor unit 25 detect different movement parameters of the arm of the user in a frequency between 50 Hz and 100 Hz. They generate movement signals from these, which are forwarded to processing unit 23. Processing unit 23 generates data from the movement signals and stores the data in data memory 24.

In addition, processing unit 23 aggregates the movement signals of the biometric sensors of sensor unit 25 into movement data, which it likewise stores in data memory 24. Evaluation module 231 of processing unit 23 filters outliers out from the movement data using a high-pass filter set to 0.3 Hz. Afterwards, it filters secondary movement data, which represent passive arm movements of the user, out from the movement data.

Figure 3:
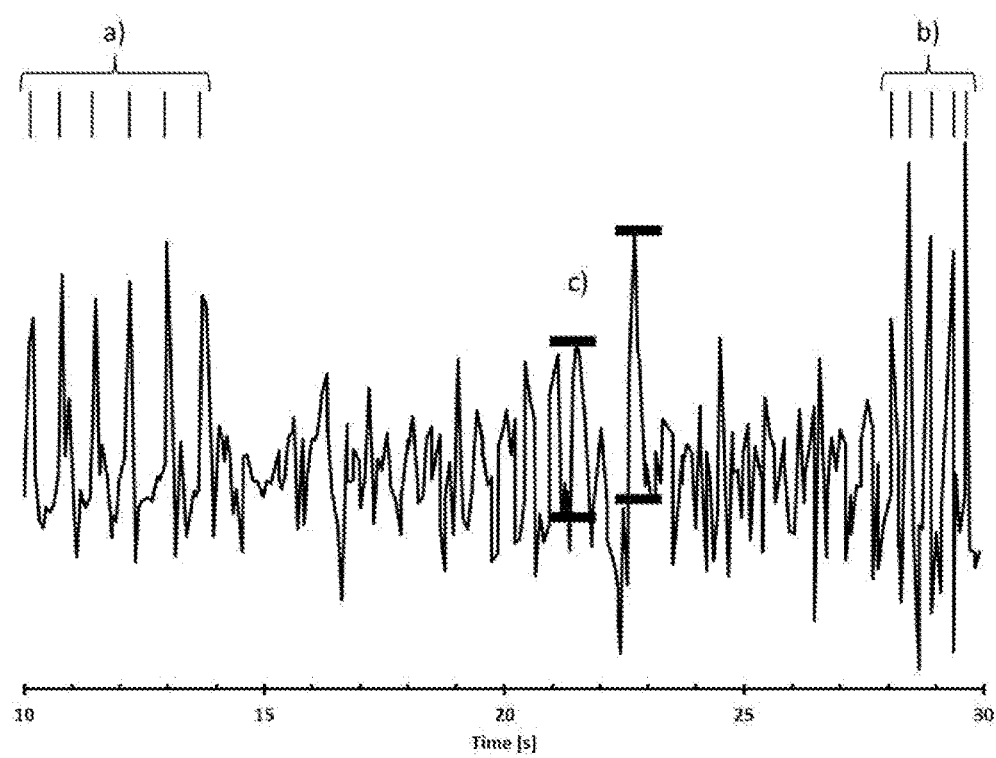
FIG. 3: a curve of movement data detected by means of the device from FIG. 1.

FIG. 3 shows a curve of unfiltered movement data. It is clear here that peaks a) occur regularly up to approximately 14 seconds, as typically occur during walking or running of the user. Evaluation module 231 of processing unit 23 correspondingly assigns a walking movement to this section and removes the associated data from the movement data. Analogously, regular peaks b) occur starting at approximately 28 seconds. This section is also filtered out as secondary movements by evaluation module 231 of processing unit 23. After the filtering, the movement data of the section between 14 and 28 seconds thus remain as primary arm movements.

During or after the filtering out, processing unit 23 continuously calculates magnitudes c) of the movement data. The magnitudes per time point correspond in each case to the square root of the sum of the squares of values in three directions of a three-dimensional coordinate system. The magnitudes are summed by processing unit 21 across a regular time window of 20 seconds to give an activity count.

In addition, a daily movement goal is defined in device 1 and stored in data memory 24. This definition is carried out via smartphone 4 when functional unit 2 and smartphone 4 are connected. A degree of achievement of the movement goal is continuously depicted on display 22. In FIG. 1 and FIG. 2, the user has achieved 43% of the daily movement goal. The movement goal may be automatically adjusted upward by processing unit 23 on the basis of the saved movement data.

In addition, the processing unit evaluates the filtered movement data, and warns the user if the evaluated movement data do not exceed a predefined threshold value over a predefined rest period. The user may additionally set functional unit 2 so that visual information is generated on display 22, an acoustic alarm is generated from speaker 282, and/or a vibration is generated by vibrator 281 as a warning.

Functional unit 21 may be set by means of smartphone 4 via the connection to smartphone 4 by means of radio interface adapter 29. In addition, the movement data and other information may be transmitted to smartphone 4. Smartphone 4 may display the movement data and further process them.

Although the invention is depicted and described in detail by means of the figures and the associated description, this depiction and this detailed description are to be understood as illustrating and exemplifying, but not limiting, the invention. In order not to embellish the invention, in certain cases well-known structures and techniques may not be shown and described in detail. Obviously persons skilled in the relevant art can make changes and modifications without exceeding the scope of the following claims. In particular, this invention covers further exemplary embodiments with any combinations of features that may deviate from the explicitly described combinations of features.

This disclosure also comprises embodiments with any combination of features that are mentioned or shown in the preceding or following with regard to different embodiments. It also comprises individual features in the figures, even if they are shown therein in connection with other features and/or not mentioned in the preceding or following. The alternatives to embodiments and individual alternatives to the features thereof described in the figures and in the description may also be excluded from the subject matter of the invention or from the disclosed subject matter. The disclosure comprises embodiments that exclusively comprise the features described in the claims or in the exemplary embodiments, as well as embodiments that comprise additional, other features.

In addition, the expression "comprise" and derivatives thereof do not exclude other elements or steps. The indefinite article "a" or "an" and derivatives thereof likewise do not exclude a plurality. The functions of several of the features listed in the claims can be fulfilled by a unit or by a step. In particular, the terms "substantially", "about", "approximately" and the like used in connection with a property or a value also define the property precisely or define the value precisely. When used in connection with a given numerical value or range, the terms "ca" and "approximately" can refer to a value or range that lies within 20%, within 10%, within 5%, or within 2% of the given value or range.

A computer program may be stored and/or distributed on a suitable medium, for example, on an optical storage medium or a solid medium, which is provided with or as part of other hardware. It may also be distributed in another form, for example, via the internet or via other wired or wireless telecommunication systems. In particular, a computer program may be, for example, a computer program product stored on a computer readable medium, which is configured to be executed in order to implement a method, in particular the method according to the invention. All reference numerals in the claims are not to be understood as limiting the scope of the claims.

Further exemplary embodiments of the present disclosure are subsequently described:

Exemplary embodiment 1 is a device for detecting and evaluating movements of a user, which comprises a processing unit, a data memory, a sensor unit with at least one biometric sensor, and a fastening device for fastening the sensor unit on an arm of the user, wherein the processing unit is configured to detect movement data from movement signals generated by the sensor unit and to store the movement data in the data memory, characterized in that the device comprises an evaluation module with which secondary movement data, which represent passive arm movements of the user, may be filtered out from the movement data.

Exemplary embodiment 2 is a device according to exemplary embodiment 1, which comprises a warning device, wherein the processing unit is configured to evaluate the filtered movement data and to activate the warning device if the evaluated movement data do not exceed a predefined threshold value across a predefined rest period.

Exemplary embodiment 3 is a device according to exemplary embodiment 2, wherein the warning device comprises a graphic display, a speaker, a vibrating structure, a muscle stimulator, or a combination thereof.

Exemplary embodiment 4 is a device according to exemplary embodiment 2 or 3, which comprises a mounting means for fastening the warning device on a finger or the ball of a thumb of the user.

Exemplary embodiment 5 is a device according to one of the preceding exemplary embodiments, wherein the evaluation module comprises a high-pass filter and/or a low-pass filter with which the movement data may be pre-filtered.

Exemplary embodiment 6 is a device according to exemplary embodiment 5, wherein the high-pass filter or the low-pass filter of the evaluation module is set to a value between 0.1 Hz and 1 Hz, and particularly to a value of approximately 0.3 Hz.

Exemplary embodiment 7 is a device according to one of the preceding exemplary embodiments, wherein the evaluation module is configured to continuously calculate magnitudes or integrals of the movement data.

Exemplary embodiment 8 is a device according to exemplary embodiment 7, wherein the movement data per time point in each case comprise values of movements in three directions of a three-dimensional coordinate system, and wherein the magnitudes each correspond to the square root of the sums of the squares of the values in the three directions of the same time point.

Exemplary embodiment 9 is a device according to exemplary embodiment 7 or 8, wherein the evaluation module is configured to process the magnitudes calculated from the movement data in a window function.

Exemplary embodiment 10 is a device according to one of exemplary embodiments 7 to 9, wherein the evaluation module is configured to identify periodic patterns in the magnitudes, which are processed using the window function, by means of Fourier transformation, preferably by means of fast Fourier transformation.

Exemplary embodiment 11 is a device according to exemplary embodiment 10, wherein the evaluation module is configured to count steps, in case a periodic pattern is identified.

Exemplary embodiment 12 is a device according to exemplary embodiment 10 or 11, wherein the evaluation module (231) is configured to count arm activities, in case no periodic pattern is identified.

Exemplary embodiment 13 is a device according to one of exemplary embodiments 7 to 12, wherein the evaluation module is configured to calculate an activity count, which corresponds to the sum of all magnitudes or integrals in a predefined time window.

Exemplary embodiment 14 is a device according to exemplary embodiment 13, wherein the predefined time window lies in a range from 0.5 seconds to ten minutes, and in particular in a range from two seconds to five minutes.

Exemplary embodiment 15 is a device according to one of the preceding exemplary embodiments, wherein the at least one biometric sensor of the sensor unit comprises an accelerometer, a gyroscope, a magnetometer, a pressure sensor, an EMG muscle sensor, or a combination of the same.

Exemplary embodiment 16 is a device according to one of the preceding exemplary embodiments, wherein the fastening device is configured for fastening the sensor unit on a finger of the user.

Exemplary embodiment 17 is a device according to one of the preceding exemplary embodiments, which comprises an interface adapter for connecting to a computer.

Exemplary embodiment 18 is a device according to exemplary embodiment 17, wherein the interface adapter is a radio interface adapter for wireless connection to the computer.

Exemplary embodiment 19 is a device according to one of the preceding exemplary embodiments, wherein the sensor unit is adjusted for sampling at a frequency of at least 10 Hz or at least 20 Hz and in particular for a range of approximately 50 Hz to approximately 100 Hz.

Exemplary embodiment 20 is a method for detecting and evaluating movements of a user, comprising: fastening a sensor unit on an arm of the user, wherein the sensor unit has at least one biometric sensor; detecting movement data from movement signals generated by the sensor unit; storing the movement data in a data memory, characterized in that the method comprises filtering secondary movement data, which represent passive arm movements of the user, out from the movement data.

Exemplary embodiment 21 is a method according to exemplary embodiment 20, which comprises an evaluation of the filtered movement data, and a warning of the user if the evaluated movement data do not exceed a predefined threshold value over a predefined rest period.

Exemplary embodiment 22 is a method according to exemplary embodiment 21, in which the warning comprises a display of visual information, an acoustic alarm, a vibration, or a combination thereof.

Exemplary embodiment 23 is a method according to one of exemplary embodiments 20 to 22, which comprises high-pass filtration and/or low-pass filtration before filtering out the secondary movement data.

Exemplary embodiment 24 is a method according to exemplary embodiment 23, wherein the high-pass filtration or the low-pass filtration is carried out at a value between 0.1 Hz and 1 Hz and in particular at 0.3 Hz.

Exemplary embodiment 25 is a method according to one of exemplary embodiments 20 to 24, wherein magnitudes or integrals of the movement data are continuously calculated during the filtering out of the secondary movement data.

Exemplary embodiment 26 is a method according to exemplary embodiment 25, wherein, during calculation of the magnitudes or integrals of the movement data per time point, each magnitude corresponds to the square root of the sum of the squares of values in the three directions of a three-dimensional coordinate system.

Exemplary embodiment 27 is a method according to exemplary embodiment 25 or 26, wherein magnitudes calculated from the movement data are processed in a window function.

Exemplary embodiment 28 is a method according to one of exemplary embodiments 25 to 27, wherein periodic patterns are identified in magnitudes, which are processed using the window function, by means of Fourier transformation and in particular fast Fourier transformation.

Exemplary embodiment 29 is a method according to exemplary embodiment 28, wherein the steps are counted, in case a periodic pattern is identified.

Exemplary embodiment 30 is a method according to exemplary embodiment 28 or 29, wherein arm activities are counted in case no periodic pattern is identified.

Exemplary embodiment 31 is a method according to one of exemplary embodiments 25 to 30, which comprises a calculation of an activity count, which corresponds to the sum of all magnitudes or integrals in a predefined time window.

Exemplary embodiment 32 is a method according to exemplary embodiment 31, wherein the predefined time window lies in a range from 0.5 seconds to ten minutes, and in particular in a range from two seconds to five minutes.

Exemplary embodiment 33 is a method according to one of exemplary embodiments 20 to 32, wherein the at least one biometric sensor of the sensor unit comprises an accelerometer, a gyroscope, a magnetometer, a pressure sensor, or a combination of the same.

Exemplary embodiment 34 is a method according to one of exemplary embodiments 20 to 33, wherein the sensor unit is fastened on a finger of the user.

Exemplary embodiment 35 is a method according to one of exemplary embodiments 20 to 34, which comprises a transmission of the filtered movement data to a computer.

Exemplary embodiment 36 is a method according to one of exemplary embodiments 20 to 35, wherein the sensor unit is adjusted for sampling at a frequency of at least 10 Hz or at least 20 Hz and in particular for a range of approximately 50 Hz to approximately 100 Hz.

Exemplary embodiment 37 is a method according to one of exemplary embodiments 20 to 36, comprising: fastening a further sensor unit on a second arm of the user, wherein the further sensor unit has at least one biometric sensor; detecting further movement data from movement signals generated by the further sensor unit; storing the further movement data in a data memory; filtering secondary movement data out from the further movement data; and comparing the filtered-out movement data to the filtered-out further movement data.

Exemplary embodiment 38 is a method according to one of exemplary embodiments 20 to 37, which comprises a definition of a movement goal, in particular a daily or weekly movement goal, and a depiction of a degree of achievement of the movement goal.

Exemplary embodiment 39 is a method according to exemplary embodiment 38, wherein the movement goal is automatically defined on the basis of stored movement data and is in particular automatically adjusted upward.

What is claimed is:

1. A device for detecting and evaluating movements of a user comprising:
    a processor configured to execute an evaluation module;
    a data memory;
    a housing with at least one biometric sensor; and
    a fastener for fastening the housing on an arm of the user,
        wherein the processor is configured to detect movement data from movement signals generated by the at least one biometric sensor and to store the movement data in the data memory, and
    wherein the evaluation module is configured to
        filter secondary movement data, which represent passive arm movements of the user, out of the movement data,
        periodically or continuously calculate magnitudes of the movement data,
        identify periodic patterns in the magnitudes of the movement data, which are processed using a window function, by means of Fourier transformation,
        count steps when a periodic pattern is identified in the magnitudes of the movement data, and
        count arm activities when no periodic pattern is identified.

2. The device according to claim 1, further comprising a warning device, wherein the processor is configured to evaluate the filtered movement data and to activate the warning device if the evaluated movement data do not exceed a predefined threshold value across a predefined rest period.

3. The device according to claim 2, wherein the warning device comprises a graphic display, a speaker, a vibrating structure, a muscle stimulator, or a combination thereof.

4. The device according to claim 2, further comprising a mounting means for fastening the warning device on a finger or a ball of a thumb of the user.

5. The device-according to claim 1, wherein the evaluation module comprises at least one of a high-pass filter or a low-pass filter with which the movement data is pre-filterable.

6. The device according to claim 5, wherein the high-pass filter or the low-pass filter of the evaluation module is set to a value between 0.1 Hertz (Hz) and 1 Hz.

7. The device of claim 6, wherein the value of the high-pass filter or the low-pass filter of the evaluation module is set to approximately 0.3 Hz.

8. The device according to claim 1, wherein the movement data for each time point comprises values of movements in three directions of a three-dimensional coordinate system, and wherein the magnitudes of the movement data correspond to a square root of sums of squares of the values of movements in the three directions at each time point.

9. The device according to claim 1, wherein the evaluation module is configured to process the magnitudes calculated from the movement data using the window function.

10. The device according to claim 1, wherein the means of Fourier transformation comprise means of fast Fourier transformation.

11. The device according to claim 1, wherein the evaluation module is configured to calculate an activity count, which corresponds to a sum of the magnitudes in a predefined time window.

12. The device according to claim 11, wherein the predefined time window lies in a range from 0.5 seconds to ten minutes.

13. The device of claim 11, wherein the predefined time window lies in a range from two seconds to five minutes.

14. The device according to claim 1, wherein the at least one biometric sensor comprises an accelerometer, a gyroscope, a magnetometer, a pressure sensor, a GPS sensor, a muscle activity sensor, or a combination of the same.

15. The device according to claim 1, wherein the at least one biometric sensor is configured to sample at a frequency of at least 10 Hertz (Hz) or at least 20 Hz.

16. The device according to claim 15, wherein the frequency at which the at least one biometric sensor is configured to sample is in a range of approximately 50 Hz to approximately 100 Hz.

17. A method for detecting and evaluating movements of a user, comprising:
    fastening a housing on an arm of the user, wherein the housing has at least one biometric sensor;
    detecting movement data from movement signals generated by the at least one biometric sensor;
    storing the movement data in a data memory;
    filtering secondary movement data, which represent passive arm movements of the user, out of the movement data;
    continuously or periodically calculating magnitudes of the movement data;
    identifying periodic patterns in the magnitudes of the movement data, which are processed using a window function, by means of fast Fourier transformation;
    counting steps when a periodic pattern is identified; and
    counting arm activities when no periodic pattern is identified.

18. The method according to claim 17, comprising:
    fastening a further housing on a second arm of the user, wherein the further housing has at least one biometric sensor;
    detecting further movement data from the movement signals generated by the further at least one biometric sensor;
    storing the further movement data in a data memory;
    filtering the secondary movement data out from the further movement data; and
    comparing the filtered movement data to the filtered further movement data.

19. The method according to claim 17, comprising defining a movement goal and displaying a depiction of a degree of achievement of the movement goal.

20. The method according to claim 19, further comprising:
    automatically defining the movement goal on the basis of the movement data stored in the data memory.

* * * * *